United States Patent [19]
Crane et al.

[11] Patent Number: 5,961,952
[45] Date of Patent: Oct. 5, 1999

[54] $^{99M}$TC-TERTIARY-BUTYL ISONITRILE AS BREAST TUMOR IMAGING AGENTS

[75] Inventors: Paul David Crane, Lincoln; David Charles Onthank, Billerica; Milind Rajopadhye, Westford, all of Mass.

[73] Assignee: DuPont Pharmaceuticals Company, Wilmington, Del.

[21] Appl. No.: 08/785,399

[22] Filed: Jan. 23, 1997

Related U.S. Application Data

[60] Provisional application No. 60/010,516, Jan. 24, 1996.

[51] Int. Cl.$^6$ ............................ A61K 51/00; A61M 36/14
[52] U.S. Cl. ............................ 424/1.65; 534/14; 424/9.1; 424/1.11
[58] Field of Search ................................ 424/1.11, 1.65, 424/9.1, 9.3, 9.4, 9.5, 9.6; 534/7, 10–16; 206/223, 569, 570

[56] References Cited

U.S. PATENT DOCUMENTS

| | | |
|---|---|---|
| 4,452,774 | 6/1984 | Jones et al. . |
| 4,707,544 | 11/1987 | Jones et al. ................................. 534/14 |
| 4,826,961 | 5/1989 | Jones et al. ................................. 534/14 |
| 4,894,445 | 1/1990 | Carpenter, Jr. et al. ................... 534/14 |
| 4,988,827 | 1/1991 | Bergstein et al. . |
| 5,081,232 | 1/1992 | Latham et al. ............................. 534/14 |
| 5,167,948 | 12/1992 | Wenzel ................................... 424/1.11 |
| 5,279,811 | 1/1994 | Bergstein et al. . |
| 5,324,824 | 6/1994 | Carpenter et al. . |

FOREIGN PATENT DOCUMENTS

| | | |
|---|---|---|
| 0183555 | 6/1986 | European Pat. Off. . |
| WO9206685 | 4/1992 | WIPO . |

OTHER PUBLICATIONS

P. Ramanathan, R.B. Patel, N. Subrahmanyam, U.N. Nayak, S.S. Sachdev and N. Ramamoorthy, *The Journal of Nuclear Medicine* 1990, 31(7), 1163–1165, "Visualization of Suppressed Thyroid Tissue by Technetium–99m–Tertiary Butyl Isonitrile: An Alternative to Post–TSH Stimulation Scanning".

Crane et al, *Journal Of Nuclear Medicine*, 1994, 35(5), 21P, "Tc–99m–Sestamibi Retention In The C–Neu Oncomouse: An In Vivo Model For Breast Tumor Imaging".

Piwnica–Worms et al, *Journal of Nuclear Medicine*, 1990, 31(7), 1166–1167, "Noncardiac Applications of Hexakis–(Alkylisonitrile) Technetium–99m Complexes".

Sachdev et al, *Nuclear Medicine Biology*, 1990, 17(6), 543–552, "Preparation and Evaluation of $^{99m}$–Tc–t–Butylisonitrile ($^{99m}$Tc–TBI) for Myocardial Imaging: a Kit for Hospital Radiopharmacy".

Bouquillon et al (1995), Nucl. Med. Biol., vol. 22, No. 5, pp. 585–588, "Synthesis Characterization and Biodistribution of a New Technetium–99m Complex with Trimethylsilylmethylisonitrile. Comparison with 99m Tc–TBI and 99m–Tc–MIBI".

Rochon et al (1996), Inorganica Chimica Acta, vol. 245, pp. 251–256 "Synthesis and Crystal Structure of Mixed–Ligand Tc(I) Complexes, with Dimethyphenylphosphine and T–Butylisonitrite".

Dox et al (1993), The Harper Collins Illustrated Medical Dictionary, p. 494 & "Tumor" and p. 301, "Neoplasm".

*Primary Examiner*—Jose' G. Dees
*Assistant Examiner*—Dameron Jones
*Attorney, Agent, or Firm*—David H. Vance

[57] ABSTRACT

A novel method of diagnosing or radioimaging breast tumors using $^{99m}$Tc- or $^{186/188}$Re-tertiary-butyl isonitrile complex and a kit for diagnosing or radioimaging breast tumors containing tertiary-butyl isonitrile and a solubilization aid are presented.

40 Claims, No Drawings

$^{99M}$TC-TERTIARY-BUTYL ISONITRILE AS BREAST TUMOR IMAGING AGENTS

This application claims the benefit of U.S. Provisional Application Ser. No. 60/010,516, filed Jan. 24, 1996.

FIELD OF THE INVENTION

The present invention relates generally to a method of using $^{99m}$Tc-tertiary-butyl isonitrile complex and its analogs as breast tumor diagnosing or imaging agents and a kit for diagnosing or imaging breast tumors.

BACKGROUND OF THE INVENTION

Several studies have reported the use of $^{99m}$Tc-sestamibi (mibi=CNCH$_2$C(CH$_3$)$_2$(OCH$_3$)) for imaging various tumors including breast, Clin. Nucl. Med. 17:171–176, thyroid, parathyroid, bone, lung and brain. $^{99m}$Tc-sestamibi appears to have a high sensitivity (>90%) and acceptable specificity (>70%) for imaging breast tumors, J. Nucl. Med. 1993, 34:149P. $^{99m}$Tc-sestamibi localizes within the mitochondria of tissues and the mechanism appears to be the attraction of the lipophilic cationic complex to the negative potential on the inner mitochondrial membrane. $^{99m}$Tc-sestamibi is retained in human tumors and is currently in clinical trial as a diagnostic agent for imaging of breast tumors.

$^{99m}$Tc-tertiary-butyl isonitrile complex ($^{99m}$Tc-TBI) has previously been described in U.S. Pat. No. 4,452,774 (Jones et al) and U.S. Pat. No. 4,988,827 (Bergstein et al). In Example 5 of Bergstein et al, it was shown that $^{99m}$Tc-TBI is an inferior myocardial imaging agent compared with the ether isonitriles described therein due to $^{99m}$Tc-TBI's low heart/liver and heart/lung uptake ratios. Bergstein et al did not test for tumor imaging agents and did not suggest using $^{99m}$Tc-TBI or $^{186/188}$Re-TBI as a breast tumor imaging agent.

Ramanathan et al, *J. Nucl. Med.* 1990, 31(7), 1163, indicate that $^{99m}$Tc-TBI can be used to image a suppressed thyroid lobe in place of the thyrotropin stimulation test. However, there is no mention in this article of using $^{99m}$Tc-TBI as a tumor imaging agent.

Even though $^{99m}$Tc-sestamibi is an excellent tumor imaging agent, other agents providing enhanced sensitivity and specificity in tumor imaging could significantly impact on patient care. This would translate to detecting smaller (earlier) tumors and/or better resolution in difficult-to-image patients. The vast number of patients diagnosed with tumors provides the impetus for finding imaging agents which provide greater uptake and retention compared with those presently known.

SUMMARY OF THE INVENTION

Accordingly, one object of the present invention is to provide a novel method of diagnosing breast tumors using $^{99m}$Tc-tertiary-butyl isonitrile complex ($^{99m}$Tc-TBI) or $^{186/188}$Re-tertiary-butyl isonitrile complex ($^{186/188}$Re-TBI) Another object of the present invention is to provide a novel method of radioimaging breast tumors using $^{99m}$Tc-tertiary-butyl isonitrile complex ($^{99m}$Tc-TBI) or $^{186/188}$Re-tertiary-butyl isonitrile complex ($^{186/188}$Re-TBI).

Another object of the present invention is to provide a novel kit for diagnosing or radioimaging breast tumors containing tertiary-butyl isonitrile, a solubilization aid, and a reducing agent capable of reducing either $^{99m}$Tc or $^{186/188}$Re to form $^{99m}$Tc-TBI complex or $^{186/188}$Re-TBI complex.

These and other objects, which will become apparent during the following detailed description, have been achieved by the inventors' discovery that $^{99m}$Tc-TBI is an excellent breast tumor imaging agent.

DETAILED DESCRIPTION OF THE INVENTION

Thus, in a first embodiment, the present invention provides a method of diagnosing breast tumors, comprising:
(a) administering parenterally to a mammal an effective amount of a composition comprising an imaging agent selected from $^{99m}$Tc-tertiary-butyl isonitrile complex and $^{186/188}$Re-tertiary-butyl isonitrile complex and a pharmaceutically acceptable carrier; and,
(b) radioimaging the mammal to determine whether a breast tumor is present.

In a preferred embodiment, the imaging agent is $^{99m}$Tc-tertiary-butyl isonitrile complex.

In a another preferred embodiment, the imaging agent is $^{186/188}$Re-tertiary-butyl isonitrile complex.

In another preferred embodiment, the composition has an activity of from about 1 to 100 mCi.

In a more preferred embodiment, the composition has an activity of from about 5 to 50 mCi.

In a another preferred embodiment, the pharmaceutical carrier is saline.

In a another preferred embodiment, the pharmaceutical carrier is water.

In another preferred embodiment, the composition contains a pharmaceutically acceptable filler.

In another more preferred embodiment, the filler is mannitol.

In another preferred embodiment, the composition used is formed from a sterile, non-pyrogenic, kit, comprising:
(a) a predetermined quantity of tertiary-butyl isonitrile;
(b) a solubilization aid; and,
(c) a predetermined quantity of a reducing agent.

In another more preferred embodiment, the solubilization aid (b) is selected from glycerin, polyethylene glycol, propylene glycol, polyoxyethylene sorbitan monooleate, sorbitan monooleate, polysorbates, poly(oxyethylene) poly (oxypropylene) poly(oxyethylene) block copolymers (Pluronics), and lecithin.

In an even more preferred embodiment, the solubilization aid (b) is selected from polyethylene glycol and Pluronics.

In a further preferred embodiment, the solubilization aid (b) is polyethylene glycol.

In another more preferred embodiment, the tertiary-butyl isonitrile (a) is in the form of a metal complex, wherein said metal is selected from Cu, Mo, Pd, Co, Ni, Cr, Ag, Rh and Zn.

In another even more preferred embodiment, the metal is Cu.

In another more preferred embodiment, the reducing agent (c) is stannous chloride.

In another more preferred embodiment, components (a), (b), and (c) are contained in a vial.

In another even more preferred embodiment, the vial contains a pharmaceutically acceptable filler.

In another further preferred embodiment, the filler is mannitol.

In a still further preferred embodiment, components (a), (b), (c), and the filler are lyophilized.

In a second embodiment, the present invention provides a method of radioimaging breast tumors, comprising:
(a) administering parenterally to a mammal an effective amount of a composition comprising an imaging agent selected from $^{99m}$Tc-tertiary-butyl isonitrile complex and $^{186/188}$Re-tertiary-butyl isonitrile complex and a pharmaceutically acceptable carrier; and, (b) radioimaging the mammal after allowing sufficient time for the composition to localize in a breast tumor present in the mammal.

In a preferred embodiment, the imaging agent is $^{99m}$Tc-tertiary-butyl isonitrile complex.

In a another preferred embodiment, the imaging agent is $^{186/188}$Re-tertiary-butyl isonitrile complex.

In another preferred embodiment, the composition has an activity of from about 1 to 100 mCi.

In a more preferred embodiment, the composition has an activity of from about 5 to 50 mCi.

In a another preferred embodiment, the pharmaceutical carrier is saline.

In a another preferred embodiment, the pharmaceutical carrier is water.

In another preferred embodiment, the composition contains a pharmaceutically acceptable filler.

In another more preferred embodiment, the filler is mannitol.

In another preferred embodiment, the composition used is formed from a sterile, non-pyrogenic, kit, comprising:

(a) a predetermined quantity of tertiary-butyl isonitrile;
(b) a solubilization aid; and,
(c) a predetermined quantity of a reducing agent.

In another more preferred embodiment, the solubilization aid (b) is selected from glycerin, polyethylene glycol, propylene glycol, polyoxyethylene sorbitan monooleate, sorbitan monooleate, polysorbates, poly(oxyethylene) poly(oxypropylene) poly(oxyethylene) block copolymers (Pluronics), and lecithin.

In an even more preferred embodiment, the solubilization aid (b) is selected from polyethylene glycol and Pluronics.

In a further preferred embodiment, the solubilization aid (b) is polyethylene glycol.

In another more preferred embodiment, the tertiary-butyl isonitrile (a) is in the form of a metal complex, wherein said metal is selected from Cu, Mo, Pd, Co, Ni, Cr, Ag, Rh and Zn.

In another even more preferred embodiment, the metal is Cu.

In another more preferred embodiment, the reducing agent (c) is stannous chloride.

In another more preferred embodiment, components (a), (b), and (c) are contained in a vial.

In another even more preferred embodiment, the vial contains a pharmaceutically acceptable filler.

In another further preferred embodiment, the filler is mannitol.

In a still further preferred embodiment, components (a), (b), (c), and the filler are lyophilized.

In a third embodiment, the present invention provides a sterile, non-pyrogenic, kit for diagnosing or radioimaging breast tumors, comprising:

(a) a predetermined quantity of tertiary-butyl isonitrile;
(b) a solubilization aid; and,
(c) a predetermined quantity of a reducing agent.

In a preferred embodiment, the solubilization aid (b) is selected from glycerin, polyethylene glycol, propylene glycol, polyoxyethylene sorbitan monooleate, sorbitan monooleate, polysorbates, poly(oxyethylene) poly(oxypropylene) poly(oxyethylene) block copolymers (Pluronics), and lecithin.

In a more preferred embodiment, the solubilization aid (b) is selected from polyethylene glycol and Pluronics.

In an even more preferred embodiment, the solubilization aid (b) is polyethylene glycol.

In another preferred embodiment, the tertiary-butyl isonitrile (a) is in the form of a metal complex, wherein said metal is selected from Cu, Mo, Pd, Co, Ni, Cr, Ag, Rh and Zn.

In a more preferred embodiment, the metal is Cu.

In another preferred embodiment, the reducing agent (c) is stannous chloride.

In another preferred embodiment, components (a), (b), and (c) are contained in a vial.

In another more preferred embodiment, the vial contains a pharmaceutically acceptable filler.

In a further preferred embodiment, the filler is mannitol.

In a still further preferred embodiment, components (a), (b), (c), and the filler are lyophilized.

As used herein $^{99m}$Tc-TBI is intended to represent the complex, $^{99m}$Tc(TBI)$_6$$^+$, formed by reduction of a $^{99m}$Tc species in the presence of TBI. $^{99m}$Tc-TBI is considered to be associated with anions present in the composition to achieve a charge neutral salt. One of ordinary skill in the art would recognize the anion(s) present depends upon the pharmaceutical carrier, the reductant used, and the presence of optional components selected from buffers, stabilization aids and lyophilization aids. If saline, for example, was used as the pharmaceutical carrier, then chloride (Cl$^-$) would be the counterion. Other anions include, but are not limited to, sulphate, acetate, phosphate, citrate, succinate and tartrate.

As used herein $^{186/188}$Re-TBI is intended to represent the $^{186/188}$Re-TBI complex formed by reduction of a $^{186/188}$Re species in the presence of TBI. As with $^{99m}$Tc-TBI, $^{186/188}$Re-TBI is considered to be associated with enough counterions necessary to achieve a charge neutral complex.

The present radiolabeled complexes are prepared by admixing TBI with a radioactive metal in suitable media at temperatures from room temperature to reflux temperatures or even higher. The labeled TBI complexes are isolable and can be obtained in high yields. The reaction is generally complete after about 1 minute to about 2 hours, depending upon the particular reagents employed and the conditions used. Reducing agents, when required or desired to speed up the reaction, are well known to those skilled in the art. Reducing agents useful in the present invention are capable of reducing a radionuclide such as Tc or Re. Examples of such well-known reducing agents include a stannous salt such as stannous chloride (often used in the form of kits), and stannous fluoride, or other suitable reducing agents such as Fe(II), Cu(I), Ti(III), or Sb(II), formamidine sulfinic acid, sodium dithionite, sodium bisulfite, hydroxylamine, ascorbic acid, sodium borohydride, and the like. The preferred reducing agent is a stannous reducing agent, more preferably, stannous chloride.

The activity of the imaging agents presently used is preferably in the range of 1 to 100 mCi, more preferably, 5 to 50 mCi. These ranges of activity are considered to be for the entire composition.

The TBI technetium complexes prepared in accord with the present invention preferably are prepared from pertechnetate, but can also be prepared from preformed technetium complexes having technetium oxidation states of, for instance, III, IV or V, by treating these preformed complexes with an excess of ligand under suitable conditions.

The TBI rhenium complexes in accord with the present invention preferably are prepared from perrhenate which is well known to those of skill in the art. Either $^{186}$Re or $^{188}$Re can be used interchangeably depending on the practioner's access to the materials necessary to obtain these isotopes.

An excess of TBI up to 100 fold molar excess or more based on the amount of radionuclide, and an excess of reducing agent, preferably 10 to 20 fold molar excess or more, can be used in the complexing reaction to ensure maximum yield from the radionuclide. The amount of reducing agent present will depend on the desired shelf life of the kit as well as other factors well known to those of skill in the art. Following the reaction, the desired complex can be separated from the reaction mixture, if required, for example by crystallization, precipitation, conventional chromatography or ion exchange chromatography; see for example U.S. Pat. No. 4,452,774, the contents of which are hereby incorporated by reference.

Preferably, the radioimaging step of the present diagnostic method is performed after allowing sufficient time for the composition to localize in a breast tumor which may be present in the mammal. One of ordinary skill in the art understands that a certain amount of time is usually needed to allow a radioimaging agent to localize and the background to diminish. The amount of time necessary depends on a number of factors known to those of skill in the art.

Kits in accord with the present invention comprise a sterile, non-pyrogenic, formulation comprising TBI and, if required, a quantity of a reducing agent for reducing a preselected radionuclide, and optionally other components such as transfer ligands, buffers, lyophilization aids, stabilization aids, and bacteriostats. The inclusion of one or more optional components in the formulation will frequently improve the ease of synthesis of the radiopharmaceutical by the practicing end user, the ease of manufacturing the kit, the shelf-life of the kit, or the stability and shelf-life of the radiopharmaceutical. The improvement achieved by the inclusion of an optional component in the formulation must be weighed against the added complexity of the formulation and added cost to manufacture the kit. Preferably, kits according to the present invention contain a solubilization aid due to the inherent difficulties of manipulating TBI.

The present kits may be contained in one or more vials and all or part of the formulation can independently be in the form of a sterile solution or a lyophilized solid. It is preferred that TBI and reducing agent be lyophilized, when possible, to facilitate storage stability. Preferably a solubilization aid is present to ease removal of TBI upon reconstitution. If lyophilization is not practical, the kits can be stored frozen or in solution at room temperature. The solvents used are usually water or saline, preferably, water. Preferably, the kits are sealed.

The choice of radionuclides for diagnostic imaging will depend on the use and can be selected from radioactive isotopes Tc, Re, Ru, Co, Pt, Fe, Os, and Ir, preferably Tc or Re. Of course, because of availability of pertechnetate generators, such radionuclide is especially preferred. Due to the emission of both beta and gamma radiation, Re can be selected for both diagnostic and therapeutic purposes. The use of $^{186/188}$Re-TBI as a therapeutic radiopharmaceutical for breast tumors is contemplated by this invention. Sterile non-pyrogenic containers (vials) which contain a predetermined quantity of sterile TBI, and a predetermined quantity of a sterile reducing agent such as stannous chloride and which are capable of reducing a predetermined quantity of a preselected radionuclide are preferred.

The TBI in the presently contemplated kits can be in the form of a non-radioactive metal adduct such as those described in U.S. Pat. No. 5,324,824, the contents of which are hereby incorporated by reference. The displaceable metals useful in the preparation of such metal-adducts are selected from the class preferably consisting of Cu, Mo, Pd, Co, Ni, Cr, Ag, Rh and Zn, and can be readily prepared by admixing a complex of the displaceable metal and TBI in a suitable media at temperatures from room temperature to reflux temperature or even higher. The reaction is generally complete after about 1 minute to about 2 hours, depending upon the reagents employed and the conditions used.

In one embodiment of the invention, a kit for use in making the complexes of the present invention from a supply of $^{99m}$Tc such as the pertechnetate solution in isotonic saline available in most clinical laboratories includes the desired quantity of TBI to react with a selected quantity of pertechnetate, and a reducing agent such as stannous chloride in an amount sufficient to reduce the selected quantity of pertechnetate to form the desired complex. In a preferred embodiment, the kit also contains a solubilization aid to aid in formation of the radioimaging complex and optionally other components such as transfer ligands, buffers, lyophilization aids, stabilization aids, and bacteriostats.

Kits according to the present invention can contain one or two vials. If two vials are used, the first vial would contain TBI, preferably a solubilization aid, and optional components selected from an inert filler, a buffer, and a stabilization aid. The second vial would contain a reductant and optional components selected from an inert filler, a buffer, and a stabilization aid such as EDTA.

A preferred kit for the facile preparation of the desired $^{99m}$Tc radiopharmaceutical, in accordance with the present invention, is comprised of one vial. The vial contains TBI and a reductant suitable to convert the $^{99m}$Tc to the desired oxidation state prepared in lyophilized form and, preferably, a solubilization aid and an inert filler, such as mannitol, to provide easy lyophilization. Additionally, a buffer may also be present in the vial. One method by which the $^{99m}$Tc radiopharmaceutical can be prepared in high yield is as follows:

A vial may be prepared containing a sterile, non-pyrogenic, freeze-dried material comprising a copper-TBI adduct at levels of 100 μg to 2 mg, or higher, a suitable reductant, such as a stannous salt (e.g., stannous chloride and its hydrates) at levels of 5 μg to 100 μg or more, with from about 1 to 250 mg, preferably, about 5 to 100 mg, of a suitable inert filler such as, but not limited to, mannitol, to provide a suitable plug after freeze-drying and, a suitable solubilization aid, such as, but not limited to, polyethylene glycol, and, optionally a buffer, such as citrate, and optionally a stabilization aid, such as cysteine. Preferably, the amount of solubilization aid present is from about 0.01 to 10 wgt %, more preferably, from about 0.05 to 5 wgt % based on the total weight of the composition of the vial. Preferably, the amount of buffer present is from about 0.1 mg to 100 mg, more preferably from 1 mg to 10 mg. Preferably, the amount of stabilization aid present is from 0.1 mg to 10 mg, more preferably from 0.5 mg to 5 mg.

The vial can be reconstituted by aseptic introduction through the rubber stopper seal using a syringe of a $^{99m}$Tc solution, preferably $^{99m}$Tc-pertechnetate in saline, in the amount of 1 mCi to 1000 mCi, preferably from 10 mCi to 100 mCi, in a volume of 0.1 mL to 10 mL, preferably 1 mL to 5 mL. The vial is then allowed to react at room temperature or it is heated at temperatures up to 100° C. or higher, for 1 minute to 6 hours, preferably it is heated at 100° C. for about 1 to 30 minutes. An effective amount of the composition is withdrawn by aseptic technique using a syringe for administration to a mammal.

Solubilization aids useful in the preparation of radiopharmaceuticals and in diagnostic kits useful for the preparation of said radiopharmaceuticals include but are not limited to glycerin, polyethylene glycol, propylene glycol, polyoxyethylene sorbitan monooleate, sorbitan monoloeate, polysorbates, poly(oxyethylene) poly(oxypropylene) poly(oxyethylene) block copolymers (Pluronics) and lecithin. Preferred solubilizing aids are polyethylene glycol and Pluronics. Preferably, the polyethylene glycol and Pluronics to be used in the present kits are of a molecular weight such that they are liquids at ambient temperature or have melting points of 60° C. or lower. Preferred number average molecular weights for polyethylene glycol are between 100 and 900, more preferably, 200, 300, 400, 500, and 600. Pluronics, also termed poloxamers, have number average molecular weights between 2000 and 15,000. Preferred number average molecular weights for Pluronics are between 2000 and 9000. The chemical and physical properties of available polyethylene glycols and Pluronics can be found in the *United States Pharmacopeia, National Formulary*, volumes XVII and XVIII.

The amount of solubilization aid will depend on the amount of TBI present in the kit, and preferably, will be present in about 0.01 to 10 wgt %, more preferably, 0.05 to 5 wgt %, based on the total weight of the composition containing the solubilization aid.

Buffers useful in the preparation of radiopharmaceuticals and in diagnostic kits useful for the preparation of said radiopharmaceuticals include but are not limited to phosphate, citrate, sulfosalicylate, succinate, tartrate, and acetate. A more complete list can be found in the *United States Pharmacopoeia*.

Lyophilization aids useful in the preparation diagnostic kits useful for the preparation of radiopharmaceuticals include but are not limited to mannitol, lactose, sorbitol, dextran, Ficoll, and polyvinylpyrrolidine (PVP).

Stabilization aids useful in the preparation of radiopharmaceuticals and in diagnostic kits useful for the preparation of said radiopharmaceuticals include but are not limited to ascorbic acid, cysteine, monothioglycerol, sodium bisulfite, sodium metabisulfite, gentisic acid, and inositol.

Bacteriostats useful in the preparation of radiopharmaceuticals and in diagnostic kits useful for the preparation of said radiopharmaceuticals include but are not limited to benzyl alcohol, benzalkonium chloride, chlorbutanol, and methyl, propyl or butyl paraben.

A component in a diagnostic kit can also serve more than one function. A reducing agent can also serve as a stabilization aid, a buffer can also serve as a transfer ligand, a lyophilization aid can also serve as a transfer ligand, and so forth.

The predetermined amounts of each component in the formulation are determined by a variety of considerations that are in some cases specific for that component and in other cases dependent on the amount of another component or the presence and amount of an optional component. In general, the minimal amount of each component is used that will give the desired effect of the formulation. The desired effect of the formulation is that the practicing end user can synthesize the radiopharmaceutical and have a high degree of certainty that the radiopharmaceutical can be safely injected into a patient and will provide diagnostic information about the disease state of that patient.

The diagnostic kits of the present invention may also contain written instructions for the practicing end user to follow to synthesize the radiopharmaceuticals. These instructions may be affixed to one or more of the vials or to the container in which the vial or vials are packaged for shipping or may be a separate insert, termed the package insert.

A "diagnostic kit," as used herein, comprises a collection of components, which may be termed the formulation, in one or more vials which are used by the practicing end user in a clinical or pharmacy setting to synthesize the radiopharmaceutical. The kit generally provides all the requisite components to synthesize and use the radiopharmaceutical except those that are commonly available to the practicing end user may be excluded, such as water or saline for injection, a solution of the radionuclide, equipment for heating the kit during the synthesis of the radiopharmaceutical if required, equipment necessary for administering the radiopharmaceutical to the patient such as syringes and shielding, and imaging equipment.

A "buffer," as used herein, is a compound that is used to control the pH of the kit during its manufacture and during the synthesis of the radiopharmaceutical.

A "lyophilization aid," as used herein, is a component that has favorable physical properties for lyophilization, such as the glass transition temperature, and is added to the diagnostic kit to improve the physical properties of the combination of the components to be lyophilized.

A "stabilization aid," as used herein, is a component that is added to the radiopharmaceutical or to the diagnostic kit either to stabilize the radiopharmaceutical once it is synthesized or to prolong the shelf-life of the kit before it must be used. Stabilization aids can be antioxidants, reducing agents or radical scavengers and can provide improved stability by reacting preferentially with species that degrade other components or the radiopharmaceutical.

A "solubilization aid," as used herein, is a component that improves the solubility of one or more other components in the formulation used for the synthesis of the radiopharmaceutical.

A "bacteriostat," as used herein, is a component that inhibits the growth of bacteria in the diagnostic kit either during its storage before use or after the kit is used to synthesize the radiopharmaceutical.

A "reducing agent," as used herein, is a compound that reacts with a radionuclide, which is typically obtained as a relatively unreactive, high oxidation state compound, to lower its oxidation state by transferring electron(s) to the radionuclide, thereby making it more reactive. Reducing agents useful in the preparation of radiopharmaceuticals and in diagnostic kits useful for the preparation of said radiopharmaceuticals include but are not limited to stannous chloride, stannous fluoride, formamidine sulfinic acid, ascorbic acid, cysteine, phosphines, and cuprous or ferrous salts. Other reducing agents are described in Brodack et. al., PCT Application 94/22496, which is incorporated herein by reference.

A "transfer ligand," as used herein, is a ligand that forms an intermediate complex with the radionuclide that is stable enough to prevent unwanted side-reactions but labile enough to be converted to the radiopharmaceutical. The formation of the intermediate complex is kinetically favored while the formation of the radiopharmaceutical is thermodynamically favored. Transfer ligands useful in the preparation of radiopharmaceuticals and in diagnostic kits useful for the preparation of said radiopharmaceuticals include but are not limited to gluconate, glucoheptonate, mannitol, glucarate, N,N,N',N'-ethylenediaminetetraacetic acid, pyrophosphate and methylenediphosphonate. In general, transfer ligands are comprised of oxygen or nitrogen donor atoms.

Other features of the invention will become apparent in the course of the following descriptions of exemplary embodiments which are given for illustration of the invention and are not intended to be limiting thereof.

Preparation of Kits, Labeling and HPLC Procedure

Tertiary-butyl isonitrile (TBI), stannous chloride dihydrate, 1-cysteine hydrochloride, and sodium hydrosulfite are commercially available from Aldrich Chemical Company. Other reagents and solvents can be obtained from other commercial sources.

The following protocol was observed for labeling, HPLC purification, and preparation of samples for assaying. A kit was prepared, as described below, and reconstituted with $^{99m}TcO_4^-$ in saline from a $^{99}Mo/^{99m}Tc$ radiopharmaceutical generator using sterile techniques well known to those skilled in the art for preparing sterile injection materials. Pertechnetate generators are well known in the art. Preferably, the generator eluant added should provide about 20–50 mCi of activity. The kit was placed in a boiling water bath for 15–25 minutes to synthesize the $^{99m}Tc$-TBI complex. Complex formation and purity was checked by TLC and HPLC (50 µL injection). A 250 µL injection was performed to collect the purified material. The fraction collected was subjected to rotary evaporation in vacuo to remove the solvent. The activity was determined using a dose calibrator. The complex was then dissolved in the appropriate media depending on the end-use.

I. Preparation of TBI Kits

A. Frozen Kit with FSA:

To a 25 mL vial was added the following: $NaH_2PO_4 \cdot H_2O$ (58 mg), formamidine sulfinic acid (FSA, $H_2NC(=NH)SO_2H$, 32 mg), ethanol (2.5 mL), saline (7.5 mL), and TBI (10 µL). The solution was stirred for 15 minutes, dispensed (in 1 mL amounts) into smaller vials, stoppered, crimped, and frozen until used.

B. Dithionite Kit:

Into an appropriate vial was transferred 0.30 mL of ethanol, then 5 µL of TBI, followed by a solution of about 15 mg of sodium dithionite (sodium hydrosulfite, $Na_2S_2O_4$) in 1 mL of saline.

C. Kit using $[Cu(TBI)_4]BF_4$:

This kit was prepared by combining the following: tetrakis(TBI)copper(I) tetrafluoroborate (1 mg), sodium citrate dihydrate (2.6 mg), L-cysteine hydrochloride monohydrate (1 mg), and 4 µL of a solution of stannous chloride dihydrate (prepared from 3 mg of $SnCl_2 \cdot 2H_2O$ in 250 µL of 1 N HCl).

Metal coordination complexes with isonitriles are well known and are described in U.S. Pat. No. 5,324,824, the contents of which are incorporated herein by reference. Examples 1–8 of this patent form metal coordination complexes of TBI.

The HPLC method for analyzing the $^{99m}Tc$-TBI complex used a Zorbax® Rx C8 column (4.6 mm×150 mm) or a Zorbax® CN (4.6 mm×250 mm), a flow rate from 1.0 to 3.0 mL/min, and a gradient mobile phase from 30% 0.05 M ammonium acetate, 70% acetonitrile to 10% 0.05 M ammonium acetate, 90% acetonitrile.

The TLC method for analyzing the $^{99m}Tc$-TBI complex was as follows:

A C-18 TLC plate (MKC 18F Reversed Phase TLC, Whatman #4803-110, 1×3", 200µ thick) was prepared by drawing lines at the 1 cm and 7 cm marks. The TLC plate was spotted with the product using a capillary. The plate was eluted up to the 7 cm mark in a 4:3:2:1 solvent mixture of acetonitrile:methanol:0.5 M ammonium acetate:THF. After drying the plate for about 5 min, it was scanned using a Bioscanner (BIOSCAN System 200 Imaging Scanner with Bioscan Auto Changer, IBM PCXT Terminal) or by an in-house radioscanner.

II. HPLC Purification of $^{99m}Tc$-TBI Complex

Purification of the $^{99m}Tc$-TBI complex, if needed, was achieved by injecting 250 µL of the product solution on a liquid chromatograph set up as described above for analyzing the complex and collecting the product fraction in a 10 mL round bottom flask (the collection time recorded) and the volatiles were removed by rotary evaporation. The activity in the flask was determined and recorded.

III. Preparation of the Screening Sample

About 5–10 mL of the appropriate media (see below) was added to the flask containing rotary evaporated $^{99m}Tc$-TBI complex and the flask rotated on a rotary evaporator (no vacuum) for about 10 min to dissolve the complex. This solution was further diluted with the media to the desired concentration. A TLC assay was performed to ensure that the product had dissolved in the medium. For cell uptake studies the medium used was RPMI-1640, Whittaker Bioproducts, Cat. #12-702B. Concentration: 200–800 µCi per 40 mL. For washout studies the medium used was saline, concentration: 3–4 mCi per 15 mL. For imaging studies the medium used was saline/PEG (polyethylene glycol), concentration: 13–25 mCi per 0.2 mL.

The use of PEG, a solubilization aid, facilitates the removal of the $^{99m}Tc$-ligand complex from the glassware used in the preparation of the complex and in its purification. It was determined that a solution of 5% PEG in saline is sufficient to remove 91% of the activity off the glassware. This amount was adequate to deliver the amount of activity needed for oncomouse imaging experiments. A solution of 5% PEG in saline has a low enough viscosity to allow for easy injection into the OncoMice™. In parallel experiments, no toxic effects from the PEG solutions were observed in mice, using concentrations below 25% (v/v).

UTILITY $^{99m}Tc$-TBI was tested in tumor cell culture assays for uptake and washout and exhibited prolonged retention in tumor cells during washout. Tumor retention in vivo was studied in the c-neu OncoMouse™. A strong correlation between breast tumor retention and tissue viability was determined for $^{99m}Tc$-sestamibi by dual label whole body autoradiography and histochemistry. $^{99m}Tc$-TBI was directly compared with $^{99m}Tc$-sestamibi for breast tumor retention in a pairwise imaging model (n=4 per compound), using planar scintigraphy with a pinhole collimator and showed significantly greater tumor retention (+133%, $p<0.01$) compared with $^{99m}Tc$-sestamibi. These results show the unpredicted utility of $^{99m}Tc$-TBI as a tumor imaging agent and the unexpected superiority of this agent compared with $^{99m}Tc$-sestamibi.

All data are expressed as the mean +/−SD, with n expressed with each data set. The imaging results were tested for significance using a paired t-test. Significance was noted at $p<0.05$ and $p<0.01$ levels.

1. Uptake Assay:

The cell uptake assay protocol was developed by Delmon-Moingeon et al.[10] Breast tumor cells (SKBR3) were incubated in media over a 2 hr time course with each test sample. This line has been identified as having high membrane potential and has been characterized for uptake of $^{99m}Tc$-sestamibi. Any compound that displays poor uptake in this isolated cell assay would not be expected to achieve high tumor levels in vivo. The first time point (10 min.) was used to compare compounds, as this was felt to represent the non-equilibrium kinetics of delivery experienced in vivo.

$^{99m}$Tc-TBI exhibited a similar pattern of uptake in all 3 cell lines tested. The results are given in Tables 1–3.

TABLE 1

Uptake (%) of $^{99m}$Tc-complexes in SKBR3 breast tumor cells.*

| Complex Ligand | 10 minutes | 20 minutes | 60 minutes |
|---|---|---|---|
| MIBI | 1.8 | 4.5 | 17.2 |
| TBI | 71.1 | 68.1 | 67 |

*Results are expressed as cell uptake (% of total). Results are given as the average of two assays. Variance ranged from 5–20%.

TABLE 2

Uptake (%) of $^{99m}$Tc-complexes in A549 lung tumor cells.*

| Complex Ligand | 10 minutes | 20 minutes | 60 minute |
|---|---|---|---|
| MIBI | 0.7 | 2.5 | 7.3 |
| TBI | 49.8 | 45.3 | 43.1 |

*Results are expressed as cell uptake (% of total). Results are given as the average of two assays. Variance ranged from 5–20%.

TABLE 3

Uptake (%) of $^{99m}$Tc-complexes in HBL100 nontransformed breast cells.*

| Complex Ligand | 10 minutes | 20 minutes | 60 minutes |
|---|---|---|---|
| MIBI | 0.9 | 3.4 | 8.8 |
| TBI | 61.3 | 62.4 | 64.3 |

*Results are expressed as cell uptake (% of total). Results are given as the average of two assays. Variance ranged from 5–20%.

2. Washout Assay:

Two cell lines are grown on cover slips: SKBR3 human breast tumor with known high membrane potential, and an epithelial cell line (CV1) of low membrane potential. Breast tumor cells (SKBR3) and normal epithelial cells (CV-1) are grown on cover slips (5×10$^5$ cells) and incubated for 60 min with 100 μCi of $^{99m}$Tc-isonitrile. The slips are then incubated for 120 min in nonisotopic medium with repeated rinses. $^{99m}$Tc activity remaining on the slips is determined at 0, 0.5, 1, 1.5, and 2 hr. Results are expressed as the ratio of tumor/normal $^{99m}$Tc activity at each of the times. Values are the mean of 4 slips per cell line.

TABLE 4

Retention of $^{99m}$Tc-isonitriles in an adherent cell assay

| Complex Ligand | Time (hr) | | | | |
|---|---|---|---|---|---|
| | 0 | 0.5 | 1 | 1.5 | 2 |
| MIBI | 38 | 36 | 34 | 29 | 26 |
| TBI | 12 | 24 | 31 | 35 | 37 |

The washout assay characterizes the retention of compounds having gained access to the cell. A significant feature of this assay is that each cover slip was given a cell count at the end of the assay, and results were corrected for actual cell density. Because of high nonspecific binding to the coverslips, early times during washout are not meaningful, and so actual uptake and pharmacokinetics during the first phase of washout are not available. The results, however, are useful in predicting prolonged retention of compounds after blood levels have cleared.

3. Whole Body Autoradiography (in vivo assay):

The test compound was given i.v. to a transgenic c-neu mouse (OncoMouse™). This mouse has been genetically constructed to spontaneously produce breast tumors. The tumors develop with the same cribriform pattern as observed in human tumors and have a similar pattern of blood supply. This model is superior to a xenograft model for testing a tumor viability imaging agent, since (a) delivery to the tissue is via a capillary system that originated with the tumor rather than secondarily to implanted cells or minces and (b) the tumor cells grow in a pattern and environment representative of that seen in humans, rather than the undifferentiated mass typical of a xenograft.

Female c-neu oncomice bearing breast adenocarcinomas >0.5 cm in diameter were injected i.v. with 1–3 mCi of $^{99m}$Tc-TBI and 5 μCi of C-14 2-deoxy-D-glucose. The mice were sacrificed at 30 min post injection by $CO_2$ inhalation. The carcass was embedded and frozen in embedding medium and 20μ frozen sections were obtained in a cryotome. Autoradiograms of sections and standards were obtained on Kodak SB5 X-ray film. Adjacent sections (5μ) were obtained and stained with hemotoxylin and eosin (H&E). Images were digitized on a LOATS video-based computerized densitometer, and regions of intersect were obtained (% ID/g).

4. Pairwise imaging in the c-neu oncomouse:

The pairwise model was designed to directly compare the images of $^{99m}$Tc-TBI with $^{99m}$Tc-sestamibi. The same mouse was imaged at two separate times within 96 hr of each other with the test compound at one time and $^{99m}$Tc-sestamibi at the other. The order of test and reference compound injected were random, but each study included at least an n=2 in each direction.

Female c-neu oncomice (18–30 g) and FVB wildtype mice were used in the pairwise studies. Mice with breast tumors between 1–15 mm were selected for imaging. Animals were anesthetized with sodium pentobarbital (IP) at a dose of 80 mg/kg. Tumors were measured with dial calipers and recorded on mouse templates. The tail was immersed in hot water for 1–2 min, wiped with alcohol, and injected via the tail vein (28 gauge insulin needle) with 5–2 mCi (0.15mL) of prepared $^{99m}$Tc-TBI. The mouse was secured in a supine position on the dissection board with limbs and head extended to expose the chest area for optimal imaging of breast tumors. All image acquisitions were performed using a Picker Digital Dyna Gamma Camera, a Siemens MicroDelta terminal/MAXDELTA system, and a custom-made 1 mm pinhole collimator mounted on the gamma camera. The general static acquisition protocol was employed, using an acquisition matrix of 256×256 pixels, in word mode. The mouse was placed at a distance of 3 cm from the surface of the dissection board to the bottom of the collimator. The anterior view of the upper torso of the animal was acquired at each time point. Consecutive images were collected starting at 10 min post injection. Six 10 min images were collected at the 3 cm distance and one 10 min image was collected of the whole body at 15 cm to determine any tail vein activity. The mouse was observed at each ten min interval for movement and administered additional anesthesia if necessary. Total activity injected was determined by measuring the syringe before and after injection, then corrected for decay back to the time of injection. The pairwise images within each study were normalized for injected dose and regions of interest were taken over breast tumors and the heart. The mean ratio of $^{99m}$Tc-TBI to $^{99m}$Tc-sestamibi in the tumor was reported.

The results of the pairwise imaging screen are shown in Table 5. $^{99m}$Tc-TBI exhibited a significant increase in tumor uptake (+133%, p<0.01) compared with $^{99m}$Tc-sestamibi. The half lives were also calculated for the washout of $^{99m}$Tc-isonitriles from SKBR3 cells. Although the kinetics were biphasic only the second phase was measureable (FIG. 4 and Table VI). $^{99m}$Tc-TBI had a 6-fold increase in $t_{1/2}$ (6-fold longer retention) compared with $^{99m}$Tc-sestamibi.

TABLE 5

Paired imaging and tumor cell washout kinetics ($t_{\frac{1}{2}}$) of test compounds

| Complex Ligand | # Animals Imaged (# Tumors) | Mean of Tumor Ratio Test/$^{99m}$Tc-sestamibi +/− Std Dev | ½ life SKBR3 Tumor Cells |
| --- | --- | --- | --- |
| MIBI | 6 (14) | 1 | 120.5 |
| TBI | 6 (14) | 1.33    +/−0.43** | 656.0 |

** p < .01

The c-neu OncoMouse™ is a useful preclinical screen for imaging breast tumors. In combination with the paired imaging model, it offers considerable potential in testing new classes of compounds for utility as tumor imaging agents.

$^{99m}$Tc-TBI had significantly increased tumor uptake and retention in vivo, relative to $^{99m}$Tc-sestamibi. Thus, $^{99m}$Tc-TBI has excellent potential as a tumor imaging agent.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letter Patent of United States is:

1. A method of diagnosing breast tumors, comprising:
   (a) administering parenterally to a mammal an effective amount of a composition comprising an imaging agent selected from $^{99m}$Tc-tertiary-butyl isonitrile complex and $^{186/188}$Re-tertiary-butyl isonitrile complex and a pharmaceutically acceptable carrier; and,
   (b) radioimaging the mammal to determine whether a breast tumor is present.
2. The method of claim 1, wherein the imaging agent is $^{99m}$Tc-tertiary-butyl isonitrile complex.
3. The method of claim 1, wherein the imaging agent is $^{186/188}$Re-tertiary-butyl isonitrile complex.
4. The method of claim 1, wherein the pharmaceutical carrier is saline.
5. The method of claim 1, wherein the pharmaceutical carrier is water.
6. The method of claim 1, wherein the composition used is formed from a sterile, non-pyrogenic, kit, comprising:
   (a) a predetermined quantity of tertiary-butyl isonitrile;
   (b) a solubilization aid; and,
   (c) a predetermined quantity of a reducing agent.
7. The method of claim 6, wherein the solubilization aid (b) is selected from glycerin, polyethylene glycol, propylene glycol, polyoxyethylene sorbitan monooleate, sorbitan monooleate, polysorbates, Pluronics, and lecithin.
8. The method of claim 7, wherein the solubilization aid (b) is selected from polyethylene glycol and Pluronics.
9. The method of claim 8, wherein the solubilization aid (b) is polyethylene glycol.
10. The method of claim 6, wherein the tertiary-butyl isonitrile (a) is in the form of a metal complex, wherein said metal is selected from Cu, Mo, Pd, Co, Ni, Cr, Ag, Rh and Zn.
11. The method of claim 10, wherein the metal is Cu.
12. The method of claim 6, wherein the reducing agent (c) is stannous chloride.
13. The method of claim 6, wherein components (a), (b), and (c) are contained in a vial.
14. A method of radioimaging breast tumors, comprising:
   (a) administering parenterally to a mammal an effective amount of a composition comprising an imaging agent selected from $^{99m}$Tc-tertiary-butyl isonitrile complex and $^{186/188}$Re-tertiary-butyl isonitrile complex and a pharmaceutically acceptable carrier; and,
   (b) radioimaging the mammal after allowing sufficient time for the composition to localize in a breast tumor present in the mammal.
15. The method of claim 14, wherein the imaging agent is $^{99m}$Tc-tertiary-butyl isonitrile complex.
16. The method of claim 14, wherein the imaging agent is $^{186/188}$Re-tertiary-butyl isonitrile complex.
17. The method of claim 14, wherein the pharmaceutical carrier is saline.
18. The method of claim 14, wherein the pharmaceutical carrier is water.
19. The method of claim 14, wherein the composition used is formed from a sterile, non-pyrogenic, kit, comprising:
   (a) a predetermined quantity of tertiary-butyl isonitrile;
   (b) a solubilization aid; and,
   (c) a predetermined quantity of a reducing agent.
20. The method of claim 19, wherein the solubilization aid (b) is selected from glycerin, polyethylene glycol, propylene glycol, polyoxyethylene sorbitan monooleate, sorbitan monooleate, polysorbates, Pluronics, and lecithin.
21. The method of claim 20, wherein the solubilization aid (b) is selected from polyethylene glycol and Pluronics.
22. The method of claim 21, wherein the solubilization aid (b) is polyethylene glycol.
23. The method of claim 22, wherein the tertiary-butyl isonitrile (a) is in the form of a metal complex, wherein said metal is selected from Cu, Mo, Pd, Co, Ni, Cr, Ag, Rh and Zn.
24. The method of claim 23, wherein the metal is Cu.
25. The method of claim 19, wherein the reducing agent (c) is stannous chloride.
26. The method of claim 19, wherein components (a), (b), and (c) are contained in a vial.
27. The method of claim 1, wherein the composition has an activity of from about 1 to 100 mCi.
28. The method of claim 27, wherein the composition has an activity of from about 5 to 50 mCi.
29. The method of claim 1, wherein the composition contains a pharmaceutically acceptable filler.
30. The method of claim 29, wherein the filler is mannitol.
31. The method of claim 13, wherein the vial contains a pharmaceutically acceptable filler.
32. The method of claim 31, wherein the filler is mannitol.
33. The method of claim 31, wherein the components in the vial are lyophilized.
34. The method of claim 14, wherein the composition has an activity of from about 1 to 100 mCi.
35. The method of claim 34, wherein the composition has an activity of from about 5 to 50 mCi.
36. The method of claim 14, wherein the composition contains a pharmaceutically acceptable filler.
37. The method of claim 36, wherein the filler is mannitol.
38. The method of claim 26, wherein the vial contains a pharmaceutically acceptable filler.
39. The method of claim 38, wherein the filler is mannitol.
40. The method of claim 38, wherein the components in the vial are lyophilized.

* * * * *